US006926686B2

(12) United States Patent
Cheatham

(10) Patent No.: US 6,926,686 B2
(45) Date of Patent: Aug. 9, 2005

(54) CERVICAL COLLAR

(75) Inventor: Melvin L. Cheatham, Ventura, CA (US)

(73) Assignee: Cheatham Consultants International Inc., Ventura, CA (US)

( * ) Notice: Subject to any disclaimer, the term of this patent is extended or adjusted under 35 U.S.C. 154(b) by 165 days.

(21) Appl. No.: 09/573,013

(22) Filed: May 17, 2000

(65) Prior Publication Data

US 2002/0156408 A1 Oct. 24, 2002

(51) Int. Cl.[7] ................................................ A61F 5/00
(52) U.S. Cl. ................................ 602/18; 128/DIG. 23
(58) Field of Search ............................ 602/17, 18, 20, 602/21, 22; 128/DIG. 23, 878, 879; 601/40; 482/444

(56) References Cited

U.S. PATENT DOCUMENTS

| 2,818,063 | A | * | 12/1957 | Smith | 602/18 |
| 3,164,151 | A | * | 1/1965 | Nicoll | 602/18 |
| 3,810,466 | A | * | 5/1974 | Rogers | 602/18 |
| 4,205,667 | A | * | 6/1980 | Gaylord | 602/18 |
| 4,232,663 | A | * | 11/1980 | Newton | 602/18 |
| 4,401,111 | A | * | 8/1983 | Blackstone | 602/18 |
| 5,060,661 | A | * | 10/1991 | Howard | 128/845 |
| 5,403,266 | A | * | 4/1995 | Bragg | 602/18 |
| 5,415,624 | A | * | 5/1995 | Williams | 602/14 |

* cited by examiner

Primary Examiner—Michael A. Brown
(74) Attorney, Agent, or Firm—Jones Day

(57) ABSTRACT

A cervical collar that will hold the chin, neck and head of the wearer in an anatomically neutral position when the wearer is in an upright or nearly upright position.

28 Claims, 3 Drawing Sheets

US 6,926,686 B2

CERVICAL COLLAR

BACKGROUND OF THE INVENTION

1. Field of the Invention

The field of this invention is cervical collars.

Specifically, this invention pertains to a cervical collar that is designed for use by travelers or others who want to be able to sleep while sitting up.

2. Background

Even the infrequent flyer has experienced the following situation. After a long day in an unfamiliar time zone, she has to rush to the airport to make the last flight home. Tired, harried and stressed out, she finally makes her way through the rush hour traffic, through the long lines at check-in and baggage inspection, through the crowds of people coming and going, and finally gets on the plane. The plane is full, and she has a center seat in coach class. Shortly after the plane lifts off, she reclines her seat but finds it doesn't recline very far, certainly not far enough to be really comfortable, and she can't lean to one side or the other without bumping into the stranger next to her. Still, she is so tired that puts her head back as far as she can and falls fast asleep. One of two things typically happens at this point. Once she falls deeply asleep, her neck no longer holds the heavy weight of her head up, so she either awakens when her head slumps forward or to the side, or, she is so tired and falls so deeply asleep that she doesn't awaken when her head slumps, but awakens some time later with a severely stiff neck (or even worse, a strained neck). Neither situation is enjoyable.

This situation is not restricted to airplanes and airplane travel. The fact is that the human head is heavy, and holding it erect requires much more neck muscle strength that healthy people realize. But in hospitals and convalescent hospitals, it is common to see people who are sitting up but cannot keep their heads erect, even if they are awake. People in convalescent hospitals often spend most of their days sitting in wheel chairs, alternatively dozing. Just like the airplane traveler described above, their heads droop, sometimes to a dangerous degree, when they do sleep.

For these reasons, small, usually inflatable travel pillows are a staple in catalogs directed to the frequent traveler. These are invariably horseshoe-shaped pillows that provide some cushioning on the sides and in the back, but not in the front. However, once the person falls asleep the head is as likely to slump forward as to the side, particularly in situations where the person cannot recline very far. Moreover, when that happens, the person's cervical spine is placed in a potentially harmful state of hyperflexion.

Therefore, there exists a need in the art for an improved cervical collar than can be used by those people who want to, or need to, sleep while in a substantially upright position, that will keep the person's head "floating" in an anatomically neutral position above the neck while they sleep.

SUMMARY OF THE INVENTION

The collar herein disclosed is designed to fit entirely around the persons head and neck—the back, both sides and under the chin—and includes an elongated portion in the front (that is, the portion that will be under the person's chin) that in use extends from the underside of the person's chin to the person's chest so that the chin is maintained during sleep in the anatomically neutral position.

In the preferred embodiment, the sides and back of the collar are substantially rectangular in cross section.

In another embodiment, the rear of the collar (that is, the portion that will be under the back of the person's head) is also elongated so as to rest against the person's back during use.

In another embodiment, the collar is openable in the front, and has a Velcro® type attachment to secure the device in place during use.

In another embodiment, the center opening of the device is somewhat angled, being narrower at the bottom and larger at the top, to more closely fit the contour of the person's neck and lower head.

Therefore, an improved cervical collar for use during sleep in a substantially upright position is disclosed.

DETAILED DESCRIPTION OF THE PREFERRED EMBODIMENTS

Figure 1:
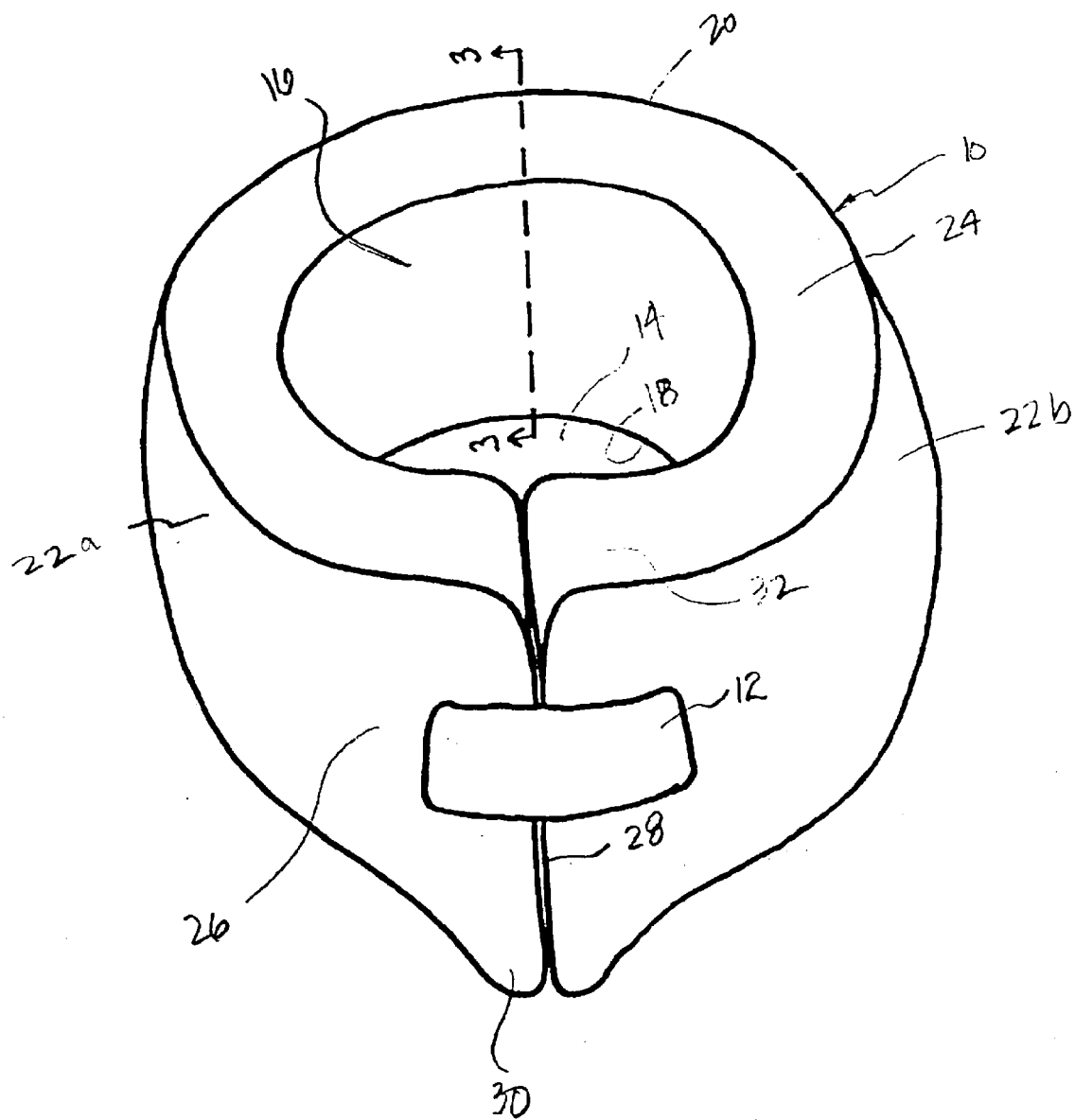
FIG. 1 is a front perspective view of one embodiment of the device in its closed position, as it would be when worn by the user, also showing the closure device on its front.

Referring to FIG. 1, the device is shown in its closed position as it would be during use. In this preferred embodiment, the device is almost entirely of one-piece construction, comprising the body 10 and the closure device 12 attached thereto. The body 10 can be manufactured as an inflatable device, that is an air bladder having a selectively openable and closable air tube (not shown) for inflating and deflating the device to the desired firmness, and for entirely deflating the device for storage. Or it can be manufactured from conventional soft material such as foam rubber or other suitably soft, non-toxic and durable material. Or it can be manufactured like a conventional pillow having an outer fabric or plastic material stuffed with any conventional material from feathers to beans to rice hulls. The device can also be fitted with a removable outer cover (not shown) that could be removed for washing, then refitted over the body 10. In that case, of course, the closure device 12 would have to be attached to the cover rather than to the body 10 itself.

The body 10 in the preferred embodiment is in a substantially round, donut-like configuration, having a central aperture 14, an interior surface 16, a bottom surface 18, a back section 20, two side sections 22a and 22b, upper section 24, and a front section 26 that is split down the middle thereof to form centered opening 28. In this embodiment, the upper section 24 is shown as being substantially flat. That, of course, is a matter of design choice. It could also be slightly or substantially rounded, for example. Also, the exterior configuration of the preferred embodiment is substantially circular in shape. The exterior configuration could be of other shapes as well, such as squared, rectangular, triangular, hexagonal, etc.

As seen in FIG. 1, the front section 26 has an elongated portion 30 that extends downwardly a sufficient distance so that the upper portion 32 of the front section 26 will contact the underside of the user's chin and the lower end of the elongated portion 30 will rest on the user's chest so as to hold the person's chin and head in the anatomically neutral position. For most people, the desired distance between the upper portion 32 and the lower end of the elongated portion 30 will be between 6 and 7 inches.

In this embodiment, the rear portion 20 and the side portions 22a and 22b are of substantially the same dimensions. For most people, the preferred dimensions are about 3 inches wide (that is, the width of the upper section 24) and about 4 inches top to bottom (that is, from upper section 24 to bottom section 18). The central aperture 14 is preferably about 5 to 6 inches in diameter, and the overall width of the device, front to back is about 12 inches. The elongated front portion 30 tapers down from the side portion 22a and 22b over a distance of about 3 to 4 inches in the preferred embodiment.

Figure 2:
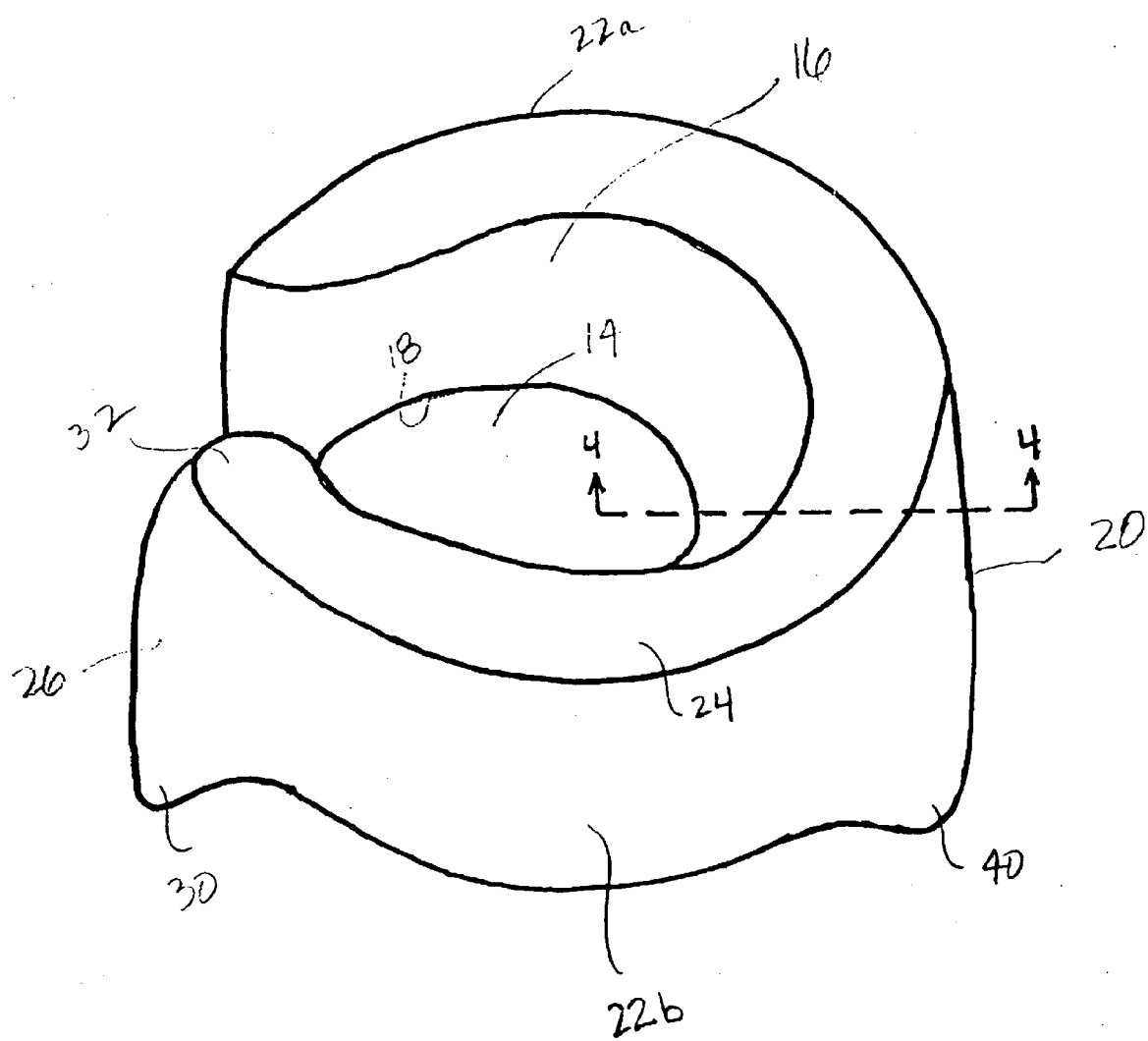
FIG. 2 is a side perspective view showing the device in the opened position before being inserted around the user's neck.
Figure 3:
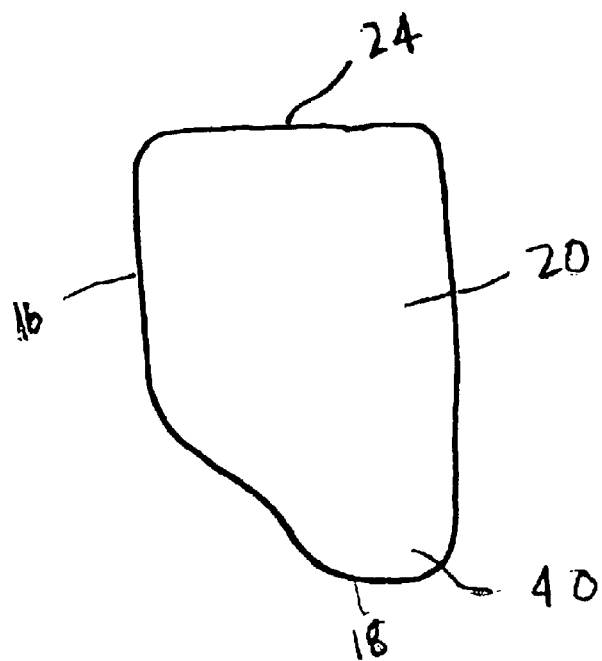
FIG. 3 is a cross-section (taken along line 3—3 in FIG. 1) showing the substantially rectangular cross sectional construction of the back (and sides) of the device, and how the rear portion of the device extends slightly down to contact the user's back in one embodiment.

FIG. 2 shows another embodiment of the invention in which the rear portion 20 has a downwardly extending section 40 that is designed and constructed so that the top or rear portion 20 contacts the back of the user's head and neck area, and the downwardly extending section 40 will contact the user's back so as to maintain the head and neck in the anatomically neutral position during use. This embodiment is shown in cross-section in FIG. 3. Alternatively or in addition, the upper portion of the rear section 20 could be elevated slightly (not shown).

Figure 4:
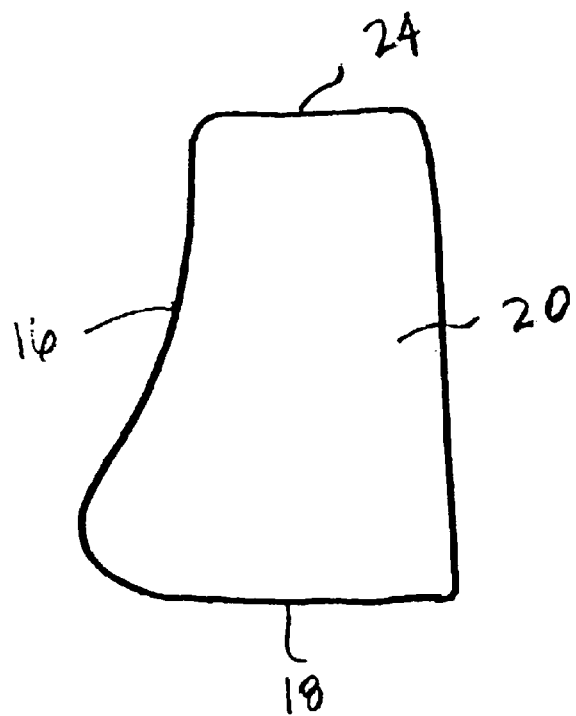
FIG. 4 is a cross-section (taken along line 4—4 in FIG. 1)showing the slightly tapered interior opening of the device in one embodiment.

In yet another embodiment, shown in cross-section in FIG. 4, the interior surface 16 is slightly contoured or tapered so as to conform more closely to the shape of the transitional area between the users head and neck.

Any and all of these aspects of the different embodiments shown can be included in the device as ultimately constructed and used.

The preferred embodiment of the closure device 12 is a strap that is sewn (or attached by other conventional means) at one end to one side of the front portion 26, and is attachable at its other end to the other side of front portion 26 by any conventional means (such as Velcro®, a button and button hole, a snap or a magnet, for example) so as to hold the two sides of front portion 26 together during use.

While different embodiments have been shown and described, it will be apparent to those skilled in the art that the invention is not limited to the specific devices shown, but is of the full breadth and scope of the following claims.

What is claimed is:

1. A cervical collar to be worn by a person while sleeping in an upright or semi-reclined position, said collar having a front section, side sections, and a back section, all defining a central aperture, in which the front section of the collar has a downwardly extending elongated portion designed and constructed to rest on the wearer's chest when in use, said front section, side sections, and back sections all designed and constructed so as to hold the chin, head and neck of the wearer of the collar in an anatomically neutral position during use without materially restricting rotational movement of the wearer's head, and wherein the collar comprises a body member that is of two-piece construction comprising a central member and a removable outer cover.

2. The device of claim 1 in which the front section of the collar is split down the middle so as to form an opening to allow easy application of the device.

3. The device of claim 2 in which the device comprises an inflatable and deflatable air bladder, the air bladder having an openable and closable air tube for inflating the air bladder to the desired firmness, and deflating the air bladder for storage.

4. The device of claim 2 including means for securing the device in a closed position.

5. The device of claim 4 in which the means for securing the device comprises a strap that is selectively attached to both sides of the front section.

6. The device of claim 5 in which the strap is sewn on one side of the front section, and attachable to the other side of the front section by conventional means, such as hook and loop, button, snap or magnet.

7. The device of claim 2 in which the rear section has a downwardly extending portion.

8. The device of claim 2 in which the real section has an upwardly extending portion.

9. The device of claim 2 in which the collar also comprises an upper portion that is substantially flat.

10. The device of claim 2 in which the collar also comprises an upper portion that is substantially rounded.

11. The device of claim 2 in which the exterior configuration of the overall device is substantially circular.

12. The device of claim 2 in which the exterior configuration of the overall device is substantially rectangular.

13. The device of claim 1 in which the device comprises an inflatable and deflatable air bladder, the air bladder having an openable and closable air tube for inflating the air bladder to the desired firmness, and deflating the air bladder for storage.

14. The device of claim 1 in which the rear section has a downwardly extending portion.

15. The device of claim 1 in which the rear section has an upwardly extending portion.

16. The device of claim 1 in which the collar also comprises an upper portion that is substantially flat.

17. The device of claim 1 in which the collar also comprises an upper portion that is substantially rounded.

18. The device of claim 1 in which the exterior configuration of the overall device is substantially circular.

19. The device of claim 1 in which the exterior configuration of the overall device is substantially rectangular.

20. A cervical collar to be worn by a person while sleeping in an upright or semi-reclined position, said collar having a front section, side sections, and a back section, all defining a central aperture, in which the front section of the collar has a downwardly extending elongated portion designed and constructed to rest on the wearer's chest when in use, said front section, side sections, and back sections all designed and constructed so as to hold the chin, head and neck of the wearer of the collar in an anatomically neutral position during use without materially restricting rotational movement of the wearer's head, and in which the central aperture is tapered, being narrower at the bottom and wider at the top.

21. A cervical collar to be worn by a person while sleeping in an upright or semi-reclined position, said collar having a front section, side sections, and a back section, all defining a central aperture, in which the front section of the collar has a downwardly extending elongated portion designed and constructed to rest on the wearer's chest when in use, said front section, side sections, and back sections all designed and constructed so as to hold the chin, head and neck of the wearer of the collar in an anatomically neutral position during use without materially restricting rotational movement of the wearer's head, in which the front section of the collar is split down the middle so as to form an opening to allow easy application of the device and in which the central aperture is tapered, being narrower at the bottom and wider at the top.

22. A cervical collar comprising:

a) a substantially doughnut-shaped configuration having a back section, two side sections, and a front section, all defining a central aperture;

b) said front section being split to provide an opening to allow easy application of the collar;

c) said front section having a downwardly extending front portion;

d) said rear section having a downwardly extending rear portion;

e) said central aperture being slightly tapered, smaller at the bottom and larger on the top; and f) means for holding the two sides of said split front section together during use.

23. A wrap-around cervical collar designed and constructed to provide comfortable support for the head of the wearer thereby allowing the wearer to sleep in an upright or semi-reclined position while the wearer's head is maintained in an anatomically neutral position, the collar comprising:

a) an elongate, flexible body member;

b) said body member having two ends, a middle section, and two side sections, one side section between each end section and each middle section, all designed and constructed such that when worn by the wearer, the two end sections come together under the wearer's chin, the back section is under the back of the wearer's head, and the two side sections are adjacent to the sides of the wear's neck;

c) said end sections each having a downwardly extending portion that is designed and constructed such that when the two ends are brought together under the wearer's chin, the downwardly extending portions rest on the wearer's chest;

d) said back section having an upwardly extending portion that is designed and constructed such that it supports the back of the wearer's head in the upright position; and e) the upper edges of said side sections and said front section being designed and constructed such that rotation motion of the wearer's head is not materially restrained; and wherein said body member is of two-piece construction, comprising a central member and a removable outer cover.

24. The device of claim 23 further comprising means for securing the two ends sections together.

25. The device of claim 24 wherein said means for securing the two end sections together are hook and loop means.

26. The device of claim 23 wherein said body member is constructed entirely of foam.

27. The device of claim 23 wherein said body member comprises an inflatable air bag.

28. The device of claim 23 wherein said body member comprises a liquid filed bag.

* * * * *